United States Patent
Rossi et al.

(10) Patent No.: US 9,861,581 B2
(45) Date of Patent: Jan. 9, 2018

(54) GRANULATE FOR THE FORMULATION OF ORODISPERSIBLE TABLETS

(71) Applicant: E-PHARMA TRENTO S.p.A., Frazione Ravina (IT)

(72) Inventors: Massimiliano Rossi, Villamontagna (IT); Riccardo Catalano, Molinda Di Fiemme (IT); Silvia Boschetti, Aldeno (IT); Paolo Andreatta, Villazzano (IT)

(73) Assignee: E-PHARMA TRENTO S.p.A., Trento (IT)

(*) Notice: Subject to any disclaimer, the term of this patent is extended or adjusted under 35 U.S.C. 154(b) by 0 days.

(21) Appl. No.: 14/828,692

(22) Filed: Aug. 18, 2015

(65) Prior Publication Data
US 2016/0045438 A1 Feb. 18, 2016

Related U.S. Application Data

(63) Continuation of application No. 12/753,571, filed on Apr. 2, 2010, now abandoned.

(30) Foreign Application Priority Data

Apr. 9, 2009 (EP) .................................. 09425135

(51) Int. Cl.
*A61K 9/16* (2006.01)
*B01J 2/16* (2006.01)
*A61K 47/26* (2006.01)
*A61K 9/20* (2006.01)
*A61K 9/00* (2006.01)

(52) U.S. Cl.
CPC .......... *A61K 9/1623* (2013.01); *A61K 9/0056* (2013.01); *A61K 9/2018* (2013.01); *A61K 47/26* (2013.01); *B01J 2/16* (2013.01)

(58) Field of Classification Search
CPC ...... A61K 9/16; A61K 9/1623; A61K 9/2018; A61K 9/0056; A61K 47/26; B01J 2/16
See application file for complete search history.

(56) References Cited

U.S. PATENT DOCUMENTS

| | | | |
|---|---|---|---|
| 5,576,014 A | 11/1996 | Mizumoto et al. | |
| 5,866,163 A | 2/1999 | Myers et al. | |
| 6,149,938 A | 11/2000 | Bonadeo et al. | |
| 6,165,511 A | 12/2000 | Schwarz et al. | |
| 6,387,402 B1 * | 5/2002 | Moraly | A61K 9/2013 264/13 |
| 2003/0002912 A1 | 1/2003 | Morpeth | |
| 2006/0025584 A1 | 2/2006 | Eroma et al. | |
| 2006/0251716 A1 | 11/2006 | Norman et al. | |
| 2007/0212417 A1 | 9/2007 | Cherukuri | |
| 2010/0178306 A1 * | 7/2010 | Kolter | A61K 9/0056 424/400 |

FOREIGN PATENT DOCUMENTS

| | | | |
|---|---|---|---|
| DE | WO 2008148733 A2 * | 12/2008 | ........ A61K 9/0056 |
| EP | 1 800 669 A1 | 6/2007 | |
| WO | WO 00/27357 | 5/2000 | |
| WO | WO 03/009830 A1 | 2/2003 | |
| WO | WO 03/051338 A1 | 6/2003 | |
| WO | WO 2007/104771 A1 | 9/2007 | |

OTHER PUBLICATIONS

Lipsanen et al., International Journal of Pharmaceutics, 345: 101-107 (2007).*
Wan et al., International Journal of Pharmaceutics, 141: 161-170 (1996).*
Bauer et al., STP Pharma Sciences, 11: 203-209 (2001).*
Suresh Bandari, et al., "Orodispersible tablets: An overview", Asian Journal of Pharmaceutics, http://www.asiapharmaceutics.info, Jan. 2008, pp. 2-11.
Technical Bulletin, Compressol SM, SPI Pharma T135-Compressol SM (Jan. 2009) http://www.spipharma.com/uploads/Compressol-SM%20T135.pdf accessed on Jun. 27, 2014.
Product Bulletin, Compressol SM, SPI Pharma PB329-CompressolSM Mar. 2009 http://www.spipharma.com/uploads/Compressol%20SM%20USP-%20PIB329.pdf accessed on Jun. 27, 2014.
Molokhia et al., Drug Development and Industrial Pharmacy, 13(9-11), 1933-1946 (1987).
Yu et al., Journal of Pharmaceutical Sciences, 87: 774-777 (1998).
U.S. Pharmacopeia Chapter 1174, Powder Flow, accessed Jan. 18, 2012.
SPI Pharma, Mannogem™ Mannitol Technical Bulletin (2007).
Ahmed and Shaikh, Pakistan Journal of Pharmaceutical Sciences vol. 16: 13-16 (2003).

* cited by examiner

*Primary Examiner* — Kortney L. Klinkel
*Assistant Examiner* — Lisbeth C Robinson
(74) *Attorney, Agent, or Firm* — Oblon, McClelland, Maier & Neustadt, L.L.P.

(57) ABSTRACT

This invention relates to a granulate comprising mannitol and sorbitol in a weight ratio of between 70:30 and 97:3. This invention also relates to the use of a granulate in the preparation of orodispersible tablets, to the orodispersible tablets obtained with a granulate and to a process of for producing a granulate.

7 Claims, 1 Drawing Sheet

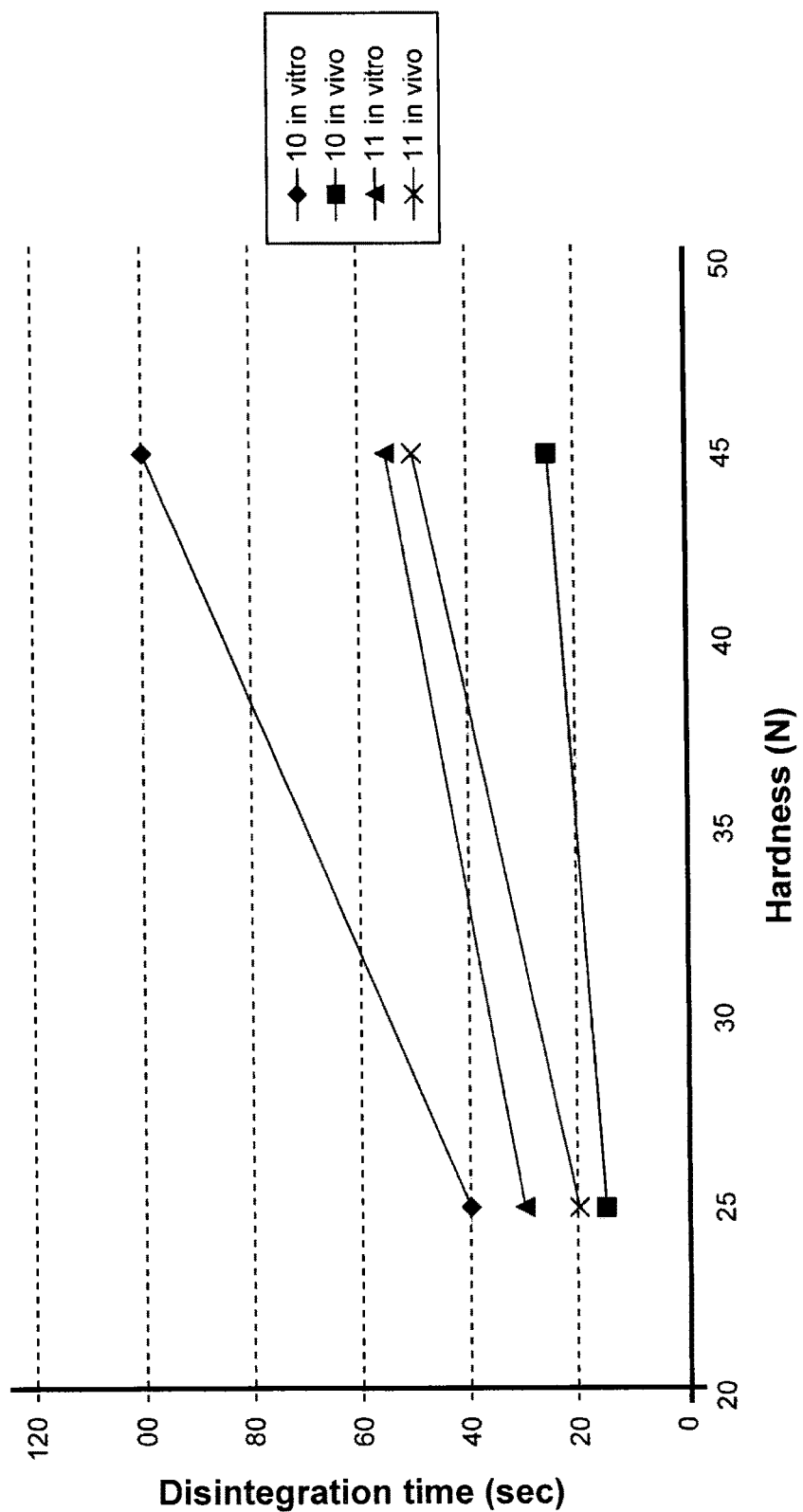

GRANULATE FOR THE FORMULATION OF ORODISPERSIBLE TABLETS

FIELD OF THE INVENTION

This invention relates to a granulate for the formulation of orodispersible tablets, in particular the formulation of orodispersible tablets comprising pharmaceutical or nutritional active ingredients.

In particular this invention relates to a granulate comprising mannitol and sorbitol in a weight ratio between 70:30 and 97:3. This invention also relates to the use of the said granulate in the preparation of orodispersible tablets, to orodispersible tablets obtained using the said granulate and to a production process for obtaining the said granulate.

The orodispersible tablets obtained using the granulate according to this invention have high porosity and may comprise a high content of the active ingredient in comparison with the orodispersible tablets known in the art.

STATE OF THE ART

Orodispersible (OD) tablets are tablets taken orally which rapidly disintegrate in the mouth through the effect of the solvent action of saliva and the mechanical action of the tongue. OD tablet formulations have better acceptability than traditional swallowable tablets, both in patients having difficulty with swallowing such conventional tablets (for example young children and the elderly), and patients with gastro-intestinal syndromes, who have greater problems in absorbing the active ingredients from solid pharmaceutical forms taken orally, which may be disturbed by the presence of the still undissolved solid tablet within the gastro-intestinal tract.

The disintegration of an OD tablet does not take place through a single mechanism, but involves various phenomena such as swelling of the disintegrant in contact with saliva, the formation of small channels promoted by the presence of pores in the tablet, the presence of effervescent substances, the mechanical action of the tongue, and so on.

In any event, the penetration of water (saliva) within an OD tablet is the first and fundamental step to disintegration, and for this it is necessary to find a compromise between the physical characteristics of the tablet and the chemical properties of the excipients used in the formulation.

U.S. Pat. No. 6,149,938 relates to a process for obtaining a useful granulate for the production of a solid form for oral use which rapidly disintegrates in the buccal cavity. This granulate is prepared by the fluidised bed granulation of an aqueous solution comprising a water-soluble or water-dispersible polymer and a polyalcohol, which may optionally be mixed with other solid components, and subsequent drying in a fluidised bed dryer. The polyalcohol preferably used is sorbitol, but others such as mannitol, xylitol, maltitol and so on may also be used; the quantity of polyalcohol varies between 50% and 90% by weight with respect to the total weight of the tablet obtained by compression of the granulate. The tablets described in the examples include lubricants, have a weight of between 1 and 2 grams, and a disintegration time of between 30 and 140 seconds.

Despite the fact that the Official Pharmacopoeia has used the term OD tablets to define tablets which disperse in the mouth within 3 minutes before swallowing, the US FDA has defined OD tablets as a solid form containing an active ingredient which disintegrates rapidly, normally in a matter of seconds, when placed on the tongue. Generally the disintegration of an OD tablet occurs between a few seconds and approximately one minute (Bandari et al., "Orodispersible tablet: An overview", Asian Journal of Pharmaceuticals, January 2008). Taking a time of 20-30 seconds as a commercially acceptable value for the definition of fast disintegration, no tablets having a mass of more than 600 mg are found on the market because increased mass makes it difficult for saliva to penetrate the tablet and therefore inhibits the function of the disintegrants, with consequent slowing of disintegration.

Conventional OD tablets (as for example described in WO 03/009830 and in WO 00/27357) always include at least one disintegrant which swells as a result of water absorption and/or water channelling. However, the presence of a disintegrant, which is necessary for the disintegration of conventional OD tablets, has two disadvantages—on the one hand it increases the mass of the tablet restricting the possibility of adding the active ingredient in larger doses, and on the other it absorbs saliva, leaving a dry feeling in the oral cavity.

EP 1 800 669 relates to a solid pharmaceutical composition comprising a central core containing the active ingredient and excipients for an orodispersible formulation and an orodispersible coating, for the oral, oral mucosal or sublingual administration of agomelatin. In more detail, the orodispersible coating is obtained with a specific diluent for orodispersible preparations, or using a conventional diluent with one or more added disintegrants. The orodispersible diluent may comprise granules obtained by the co-atomization of lactose and starch (Strarlac®), or a atomized polyalcohol, for example sorbitol or mannitol, or a atomized mixture based on polyalcohols, for example excipients commercially marketed such as Partek® and Pharmaburst®. In OD tablets prepared using this method and described in the examples the polyalcohol used is mannitol for direct compression or Starlac®. The tablets obtained using this method have a maximum weight of 350 mg and in vitro tests describe a disintegration time of less than 3 minutes.

The methods of preparation described above for the production of OD tablets (for example in WO2007/104771 and U.S. Pat. No. 5,866,163) include both methods used for the production of conventional tablets and alternative methods, such as fusion or lyophilisation processes in moulds, which are already known to those skilled in the art. The production of OD tablets requires suitably designed manufacturing units because of the poor mechanical properties of the tablets. Lubricants have to be added to increase the compressibility and flowability of the powders, but there is the disadvantage that these excipients reduce the wettability of the tablet and therefore the rate of disintegration.

SUMMARY OF THE INVENTION

The object of this invention is to provide a granulate for the formulation of orodispersible tablets which overcomes the problems described.

In the course of extensive experimentation the Applicant has had to make a selection of components considering various parameters such as, for example, speed and safety of manufacture, compressibility, palatability, stability, food intolerances, solubility, purchase cost and availability on the market.

The Applicant has found that a granulate comprising mannitol and sorbitol in a specific weight ratio makes it possible to manufacture OD tablets which disintegrate rapidly, in times less than 30 seconds, in contact with saliva in the oral cavity, with good palatability.

Surprisingly the Applicant has found that the granulate according to this invention obtained from the combination of mannitol and sorbitol, two readily available and inexpensive polyalcohols, has made it possible to obtain an OD tablet which at the same time disintegrates and/or dissolves in the oral cavity without the need to add a disintegrant.

The absence of disintegrants and the presence of polyalcohols ensures that the tablets are more palatable. In fact in conventional OD tablets the quantity of disintegrant is such that it completely absorbs the saliva present in the oral cavity, because the water absorbtion capacity of these excipients varies between 3 and 10 times their weight, leaving the patient treated with a feeling of dryness in the mouth (plaster effect).

Mannitol and sorbitol are highly hygroscopic and soluble in water, which is essential for oral administration where the quantity of liquid (saliva) available for disintegration is fractions of a milliliter.

The Applicant has surprisingly found that OD tablets obtained with the granulate according to this invention may have a very much greater mass, up to 2000 mg and even more, in comparison with conventional OD tablets comprising a disintegrant, whilst keeping disintegration times below 30 seconds.

The Applicant has therefore observed that the possibility of obtaining tablets having a mass of more than 2 g also includes the possibility of adding a greater quantity of the active ingredient to the formulation in comparison with conventional tablets.

In addition to this, the increase in tablet size makes it possible to apply less pressure per unit surface area during the compression step, and as a consequence to obtain greater porosity.

The Applicant has found that the granulate according to this invention has good mechanical properties, with high compressibility and flowability, which means that it can be used without the addition of lubricating agents.

Thus, in a first aspect, this invention relates to a granulate of a mixture of mannitol and sorbitol in a ratio by weight of between approximately 70:30 and approximately 97:3.

The Applicant has found that use of the granulate according to this invention makes it possible to obtain tablets with a high compressibility index. The compressibility index is given by the ratio between the hardness of the tablet and the compression force. For the same compression force the tablets obtained using the granulate according to this invention have greater hardness and lower density. Greater hardness imparts the necessary strength upon the tablet to withstand mechanical stresses during the processes of production and packaging without breaking up. Lower density imparts greater porosity on the tablet and therefore a greater rate of disintegration because water penetrates within the OD tablet more quickly.

Thus, in a second aspect, this invention relates to an OD tablet comprising a granulate of a mixture of mannitol and sorbitol in a ratio by weight of between approximately 70:30 and approximately 97:3.

The Applicant has also observed that the characteristics of the granulate according to this invention are advantageously obtained through a fluidised bed granulation process by controlling the dimensions of the mannitol and sorbitol particles, the quantity of water, and the temperature and humidity of the air used in the granulation process.

Thus, in a third aspect, this invention relates to a process for producing a granulate comprising mannitol and sorbitol, the said process comprising the following steps:

(i) providing mannitol and sorbitol in the form of powder, preferably having an average particle size of less than 100 µm and between 200 µm and 250 µm respectively, (ii) providing a mixture of the said mannitol and the said sorbitol in a ratio by weight of between approximately 70:30 and approximately 97:3, (iii) introducing the said mixture into a fluidised bed granulator, (iv) granulating the said mixture under the following conditions:

(a) spraying a quantity of water of between 5% and 35% by weight with respect to the weight of the said mixture, and (b) introducing air at a temperature below 80° C. with a moisture content of less than 5000 ppm, preferable equal to or lower than 1000 ppm.

BRIEF DESCRIPTION OF THE FIGURES

FIG. 1 shows the in vitro and in vivo disintegration times of tablets 10 according to the invention as a function of hardness, and comparison tablets 11 described in Example 5 below.

DETAILED DESCRIPTION OF THE INVENTION

In at least one of the aforesaid aspects this invention may show one or more of the preferred characteristics described below.

Preferably the granulate according to this invention comprises mannitol and sorbitol in a ratio by weight of between 80:20 and approximately 95:5, and even more preferably approximately 90:10.

Advantageously the granulate according to this invention has an average particle size of between 50 µm and 500 µm, preferably between 150 µm and 350 µm. For values below 50 µm the granulate tends to become compacted because of prevalence of weak forces (of the Van der Waals, dipole-dipole and hydrogen bond type) over the weight force of the particle and low flowability problems occur. At values over 500 µm the granulate shows an increase in the inter-particle empty spaces, which increases the apparent volume. Apparent volume is defined as the space occupied by a particular quantity of granulate when poured and caused to fall into a container of cubic or rhomboidal shape. As the apparent volume increases, there is an increase in flow time, the time which reflects the ease of which the granulate becomes distributed in the container. As the apparent volume and flow time increase, the variability in the time required by the granulate to fill the rhomboidal container and the cubic container increases.

According to a preferred aspect the granulate according to this invention has a density of less than 1 $g/cm^3$, and more preferably less than 0.75 $g/cm^3$.

The low density of the granulate is an indication of its high porosity, and makes it possible to obtain OD tablets with reduced disintegration times, increased hardness (imparting the ability to withstand mechanical stresses) and good compressibility.

Advantageously the granulate according to this invention has a very low residual moisture content, less than 0.20% by weight relative to the weight of the granulate. More preferably the granulate according to this invention has a residual moisture content equal to or lower than 0.10% by weight relative to the weight of the granulate.

The Applicant has observed that for residual moisture values slightly above that specified (up to 0.50%) there are increases in the hardness of the tablets over time which have an adverse effect on the rate of disintegration in the mouth, while at residual moisture values well beyond those specified (up to 1.00% and more) the stability of the final tablet is compromised.

The granulate according to this invention is prepared using a fluidised bed granulation technique. Under specific conditions this type of granulation makes it possible to obtain the product with the desired characteristics.

The process of producing the granulate according to this invention comprises the following steps:
(i) providing mannitol and sorbitol in the form of powder, preferably having an average particle size of less than 100 µm and between 200 µm and 250 µm respectively,
(ii) providing a mixture of the said mannitol and the said sorbitol in a ratio by weight of between approximately 70:30 and approximately 97:3,
(iii) introducing the said mixture into a fluidised bed granulator,
(iv) granulating the said mixture under the following conditions:
(a) spraying a quantity of water of between 5% and 35% by weight with respect to the weight of the said mixture, and
(b) introducing air at a temperature below 80° C. with a moisture content of less than 5000 ppm, preferable equal to or lower than 1000 ppm.

The Applicant has observed that the use of a mixture of mannitol and sorbitol having an average mixture particle size of less than 200 µm, preferably between 100 µm and 150 µm, makes it possible to obtain a final granulate having a greater compressibility index. Because mannitol is always the main component in the mixture (in a quantity of between 70% and 97% by weight) with respect to sorbitol, which is always the secondary component (in a quantity between 30% and 3% by weight), the latter may also be used in the form of a powder having an average particle size of more than 200 µm. In particular the Applicant has found that better results are obtained with a mixture comprising mannitol having an average size of less than 100 µm and sorbitol having an average size between 200 µm and 250 µm.

In addition to this, the Applicant has observed that the use of water as a solvent makes it possible a better granulation and workability of the two polyalcohols, in addition to being non-toxic and non-hazardous.

Advantageously the preferred quantity of water is between 10% and 30% by weight, more preferably between 15% and 25% by weight with respect to the weight of the mixture of mannitol and sorbitol in the said mixture.

Preferably the temperature of the air introduced into the fluidised bed granulator is higher than 60° C., more preferably between 65° C. and 75° C., and even more preferably around 70° C. The relative moisture content of the air introduced into the fluidised bed granulator is less than 5000 ppm, preferably equal to or lower than 1000 ppm.

The Applicant has observed that temperatures equal to or higher than 80° C. may cause chemical and physical changes in the granulate, with the occurrence of fusion and yellowing. On the other hand the Applicant has observed that temperatures below 60° C. would require long drying times, which, although in principle practicable, are not convenient from the industrial point of view. In particular the Applicant has observed that optimum drying times from the industrial point of view are less than 30 minutes, preferably equal to or lower than 20 minutes. The choice of relative humidity values for the air introduced into the fluidised bed granulator also depends on drying temperature and times, and the desired residual moisture content.

The granulate obtained through the process according to this invention has perfect flowability and has a regular particle size which permits precise dosing.

The granulate obtained through the process according to this invention also has high compressibility.

Compressibility is measured as the ratio between the hardness of the tablet and the compression force applied in order to obtain that hardness. This ratio is defined as the "Compressibility Index" (CI).

The Applicant has found that the granulate according to this invention has a compressibility index of more than 4.5, a value which is not found with other known excipients for the production of orodispersible tablets.

A high CI value means that greater hardness can be obtained with less compression force. This avoids the addition of a lubricant among the excipients, which, as known to those skilled in the art, is used to prevent the granulate to stick to the punches and walls of the mould during the compression step and ensures that the particles comprising the granulate can flow.

Applying less compression forces also means obtaining a lower density and as a consequence greater porosity in the tablet so obtained. This means a greater rate of water penetration and a shorter disintegration time.

Other factors being the same, the possibility of obtaining greater hardness imparts better mechanical properties on the tablets, which ensures less problems during the steps of production and packaging of the final pharmaceutical form.

This invention also relates to an OD tablet comprising the granulate according to this invention.

Advantageously the tablet according to this invention comprises at least 50% by weight of granulate, preferably between 50% and 99% by weight. The presence of a quantity of granulate of more than 50% by weight ensures a good compression yield regardless of the mechanical characteristics of the active ingredient used, and makes it possible to achieve good compression yields even with difficulty compressible active ingredients. Below this percentage the compression yield may decrease appreciably because of the lack of contact between the particles of the granulate according to this invention.

The Applicant has also observed a further advantage of the tablets according to this invention which is correlated with the absence of disintegrants.

In general it is observed that for constant compression and hardness tablets show a decrease in density corresponding to an increase in weight, and therefore an increase in their volume and porosity. Technically, if the values of density (Y) and weight (X) of a tablet obtained at constant pressure are plotted on a system of coordinates it will be observed that the resulting straight line has a negative angular coefficient. Lines which are all parallel to each other are obtained for different pressure values.

In conventional tablets which contain disintegrants the increase in mass has nevertheless a limit associated with both the length of the route which the water (saliva) has to travel in order to penetrate within the tablet and promote the disintegrant's swelling mechanism, and the quantity of water (saliva) available within the oral cavity.

On the contrary the phenomenon of increased porosity with increased volume results in an advantage for tablets according to this invention.

The Applicant has in fact observed that using the granulate according to this invention the mass of the tablets is greater, and the rate of disintegration is also greater. This happens because disintegration of the tablet according to the invention depends only on contact between the granulate and water (saliva). Because the latter can penetrate the tablets with greater porosity more quickly, the volume and as a consequence the mass of the tablets can be increased without a corresponding increase in disintegration times.

The tablets according to this invention may comprise any active ingredient which is suitable for oral administration. Examples of the active ingredients which may be advantageously used in preparing tablets according to this invention are non-steroidal anti-inflammatory drugs (NSAIDs), anxiolytics, antiemetics, antihistaminics, proton pump inhibitors, and so on.

The active ingredients formulated in OD tablets may advantageously be coated with one or more layers of a polymer, either to mask the unpleasant taste of the active ingredient or to obtain gastric protection or prolonged/delayed release over time. Examples of polymers which are advantageously used to coat the active ingredients used in preparation of the tablets according to this invention are for example Eudragit (Evonik), Methocel (Dow), Kollicoat (BASF), Klucel (Signet), Aqualon, Aquacoat, Lustreclear (FMC), Opadry (Colorcon), Spectracel, Spectrablend (Sensient).

These polymeric coatings are fragile in the compression step. The compression materials and methods conventionally used requires high compression forces which can compromise the integrity and as a consequence the function of the coating. As a result of its high compressibility the granulate according to this invention makes it possible to reduce the risk of breakdown of the polymer coating because no high compression force is required. In particular the Applicant has observed that the granulate according to this invention has an ultimate strength which is five times less than the ultimate strength for the coating polymer.

In addition to this the use of a high percentage of granulate according to this invention, equal to at least 50% of the weight of the tablet, reduces adhesion phenomena by limiting contact between the granules of coated active ingredient and as a consequence the coating function is not compromised.

The tablet according to this invention may also comprise other ingredients typically used in the preparation of orodispersible tablets such as for example diluents, sweeteners, flavourings and the like.

Examples of suitable diluents comprise lactose, starch, dextrose, xylitol, and so on.

Examples of suitable sweeteners comprise aspartame, saccharin, acesulphame, and so on.

Examples of suitable flavourings comprise grapefruit flavour, raspberry flavour, lemon flavour, orange flavour, caramel flavour, vanilla flavour, cream flavour, and the like.

The following examples are intended to illustrate preferred aspects of the invention, without nevertheless having the object of restricting it. Those skilled in the art will be able to find various modifications which fall within the spirit of the invention and the scope of the claims.

EXAMPLE 1

A mixture of powdered mannitol (average size less than 100 µm) and powdered sorbitol (average size between 200 µm and 250 µm) in a weight ratio of 9:1 was used to prepare the granulate using different granulation methods.

Using the dry granulation technique, the mixture was first compacted by a tablet press into slugs having a diameter of approximately 20-30 mm. Using different compression forces, slugs $T_A$, $T_B$, $T_C$ having respective hardness of 20N, 50N and 120N were obtained. The slugs were then broken up using an oscillating granulator and sieved through a 1000 µm sieve. Granulates A, B and C obtained from slugs $T_A$, $T_B$, $T_C$ respectively had the average sizes and densities indicated in Table 1.

Using the wet granulation technique, the mixture was wet granulated with purified water in an Erweka AR400 granulator. The paste was dried on a fluidised bed and sieved through a 1000 µm mesh. Granulate D had an average size and density as indicated in Table 1 below.

Using the fluidised bed technique, the mixture was introduced into a Glatt WCG-CD200 fluidised bed granulator together with dry hot air at 70° C. (residual moisture content less than 1,000 ppm) and purified water was sprayed in a quantity of approximately 20% by weight with respect to the weight of the mixture. Granulate E had an average size and density as indicated in Table 1 below.

TABLE 1

| Granulate | Density | Average size |
|---|---|---|
| A | 0.606 | 259 |
| B | 0.645 | 234 |
| C | 0.714 | 231 |
| D | 0.921 | 221 |
| E | 0.513 | 242 |

The five granulates A-E so obtained were used to prepare respectively five tablets 1-5 in a dose of 2.6 g in a tablet press equipped with punches having a diameter of 25 mm exerting a compression force of 65 KN. The hardness and thickness values for the tablets so obtained are shown in Table 2 below.

TABLE 2

| Tablet | Hardness (N) | Thickness (mm) |
|---|---|---|
| 1 | 90 | 4.6 |
| 2 | 90 | 4.6 |
| 3 | 100 | 4.5 |
| 4 | 160 | 4.3 |
| 5 | 300 | 4.6 |

The data in Table 2 clearly show that granulate E according to this invention makes it possible to obtain tablets with a greater hardness for the same compression force.

EXAMPLE 2

Granulate E according to this invention was compared with a series of commercial excipients ready for compression. The comparison was made by comparing a series of tablets as described in Example 1 and measuring the resulting hardness of each tablet obtained. The results are summarised in Table 3 below.

TABLE 3

| Excipient | Hardness (N) | CI |
|---|---|---|
| Granulate E | 300 | 4.62 |
| Xylitab 200 (Danisco) | 285 | 4.38 |
| Sorbitol (Roquette) | 245 | 3.77 |
| Maltodextrin | 215 | 3.31 |
| Isomalt (Diamalt) | 214 | 3.29 |
| Emdex (Mendell) | 212 | 3.26 |

TABLE 3-continued

| Excipient | Hardness (N) | CI |
|---|---|---|
| Ercawax 4000 (Erca) | 196 | 3.02 |
| Pearlitol (Roquette) | 163 | 2.51 |
| Lactose DC | 105 | 1.62 |
| Microtal (T&L) | 92 | 1.42 |
| Saccharose | 75 | 1.15 |
| Fructose | 50 | 0.77 |
| Citric acid | 45 | 0.69 |

The data in Table 3 showed that granulate E has the best compressibility index (CI) in comparison with the excipients known in the art.

EXAMPLE 3

Granulate E according to this invention was prepared following the procedure described in Example 1, varying the process conditions (temperature and humidity) of the air. The results are summarised in Table 4 below.

TABLE 4

| Temperature (° C.) | Relative humidity (%) | Result |
|---|---|---|
| 80 | 0.1 | Non-conforming product- product melted and turned to yellow |
| 70 | 0.1 | Optimum product - moisture content 0.1% after 20 minutes drying |
| 50 | 0.1 | Non-conforming product - product moisture content 0.25% after 50 minutes drying (long) |
| 70 | 1 | Conforming product - product moisture content 0.20% after 60 minutes drying (long) |
| 70 | 10 | Conforming product - product moisture content 0.20% after 70 minutes drying (long) |
| 70 | 25 | Non-conforming product - product moisture content 0.25% after 70 minutes drying (long) |

EXAMPLE 4

Three test granulates F-H were prepared using the procedure described in Example 1, but varying drying times so as to obtain a different residual moisture content, as shown in Table 5.

TABLE 5

| Granulate | Time (minutes) | Residual moisture content (%) |
|---|---|---|
| F | 20 | 0.11 |
| G | 10 | 0.26 |
| H | 0 | 0.78 |

The three granulates F-H so obtained were used to prepare three lots of tablets 6-8 respectively with a dosage of 2.6 g in a tabletting machine having punches of diameter of 25 mm exerting a compression force of 65 KN. The hardness values of the tablets so obtained were measured immediately after preparation (T0), after one month (T1), and after three months (T3). Table 6 below summarises the values obtained.

TABLE 6

| Tablet | Hardness (N) | | |
|---|---|---|---|
| | T0 | T1 | T3 |
| 6 | 291.6 | 300.4 | 288.7 |
| 7 | 290.0 | 331.2 | >350 |
| 8 | 294.1 | * | * |

* The tablet in lot 8 was already degraded at one month

The data in Table 6 clearly showed that the residual moisture content of the granulate has an appreciable effect on the hardness of the tablets over time. The tablets in comparison lots 7 and 8 proved unusable one month and/or three months after preparation. The increased hardness of the tablets in lot 7 had an adverse effect on the disintegration rate in the mouth while the tablets in lot 8 were already degraded after one month. The tablets in lot 6 obtained from granulate according to this invention showed constant values for hardness over time and no degradation.

EXAMPLE 5

Granulate E according to this invention was used to prepare tablets of different hardness in the presence or absence of disintegrants as shown in Table 7.

TABLE 7

| Ingredients (mg) | Tablet | | | |
|---|---|---|---|---|
| | 10a | 10b | 11a | 11b |
| Granulate E | 1000 | 1000 | 925 | 925 |
| Avicel PH200 | — | — | 50 | 50 |
| Kollidon CL | — | — | 25 | 25 |
| Hardness (N) | 25 | 45 | 25 | 45 |

The disintegration time for each tablet was measured using the in vitro method according to the European Pharmacopeia, and the in vivo method. The results are summarised in Table 8 below.

TABLE 8

| Tablet | Hardness | Disintegration time (seconds) | |
|---|---|---|---|
| | | In vitro method | In vivo method |
| 10a (i) | 25 | 40 | 15 |
| 10b (i) | 45 | 100 | 25 |
| 11a (c) | 25 | 30 | 20 |
| 11b (c) | 45 | 55 | 50 |

The data in Table 8 showed that the in vitro method according to the European Pharmacopoeia does not predict the in vivo behaviour of tablets 10 according to this invention.

In fact, in vitro tablets 10 according to the invention showed an increase in disintegration time with increased hardness (from 40 to 100 seconds) and in all cases always longer than the disintegration time of comparison tablets 11 (30 and 55 respectively). Wholly negative results were also expected from the in vivo test following these results.

Vice-versa, in vivo, comparison tablets 11 behaved consistently with the in vitro results, with similar disintegration times (20 and 50 respectively), while tablets 10 according to the invention showed completely different and positive disintegration times, much shorter than those for tablets 11 (15 and 25 respectively).

The graph in FIG. 1 shows the different trends shown by tablets 10 according to the invention and comparison tablets 11, in vitro and in vivo respectively, with increasing hardness.

EXAMPLE 6

Granulate E according to this invention was used to prepare two series of tablets in the presence or absence of disintegrants as shown in Table 9. The tablets used in the test were produced in order to simulate a tablet containing an active ingredient (not actually present) which would require a coating (for example in order to mask its unpleasant flavour). Syloid FP, sodium lauryl sulphate, stearic acid and Eudragit Epo were used to prepare the polymer coating.

TABLE 9

| | Tablet | |
|---|---|---|
| Ingredients (mg) | 12 (c) | 13 (i) |
| Base for deposition of the active ingredient | | |
| Polysorbate 20 | 1.0 | 1.0 |
| Simeticone dry | 1.0 | 1.0 |
| Sugar spheres 60 | 250.0 | 250.0 |
| Coating film | | |
| Syloid FP | 30.2 | 30.2 |
| Sodium lauryl sulphate | 4.0 | 4.0 |
| Stearic acid | 6.0 | 6.0 |
| Eudragit Epo | 40.3 | 40.3 |
| Disintegrants | | |
| Avicel pH200 | 75.0 | — |
| Kollidon CL | 25.0 | — |
| Other excipients | | |
| Aspartame | 15.0 | 15.0 |
| Caramel flavour | 20.0 | 20.0 |
| Granulate E | 532.4 | 632.4 |
| Total weight | 1,000.0 | 1,000.0 |

(i) Invention
(c) Comparison

Tablets 12 and 13 were used in a test panel of 25 volunteers to check the in vivo disintegration rate and to have an objective evaluation of the palatability of the product. The organolectic characteristics about which the participants in the test had to give their opinion were the following:
  ease of swallowing
  dry feeling in the mouth
  persistent presence of residue
  ease of disintegration
  overall satisfaction In order to express their feelings the participants in the test were instructed to use the scale shown in Table 10 and to take the tablets without water and without chewing. The tablets were distributed blind.

TABLE 10

| Score | Meaning |
|---|---|
| 0 | None |
| 1 | Very little |
| 2 | Little |
| 3 | Some |

TABLE 10-continued

| Score | Meaning |
|---|---|
| 4 | Much |
| 5 | Very much |

Table 11 below shows the results obtained.

TABLE 11

| | 13 (i) | | 12 (c) | |
|---|---|---|---|---|
| | Average value | Standard deviation | Average value | Standard deviation |
| Disintegration time (sec) | 11.5 | 3.3 | 20.0 | 4.7 |
| Ease of swallowing | 4.8 | 0.4 | 4.5 | 0.7 |
| Dryness of the mouth | 0.5 | 0.7 | 1.9 | 0.9 |
| Presence of residue | 0.4 | 0.7 | 1.2 | 0.9 |
| Ease of disintegration | 4.9 | 0.3 | 4.5 | 0.5 |
| Overall satisfaction | 4.8 | 0.5 | 4.1 | 0.7 |

The results were collected and analysed by statistical processing using the t test (two tail $\alpha=0.05$) through which the means of the values obtained can be compared. Given a first value for the mean and its standard deviation, this method can be used to check whether this first mean value differs from another mean value obtained. The disintegration time for tablets 13 according to the invention proved to be significantly less than the disintegration time for comparison tablets 12 containing disintegrants. In addition to this, tablet 13 according to the invention proved to be more acceptable overall, with a disintegration time of almost 50% less than that of comparison tablet 12.

The invention claimed is:

1. A process for the production of a granulate consisting of mannitol and sorbitol, comprising:
   (i) providing mannitol and sorbitol in the form of powder,
   (ii) mixing said mannitol and the said sorbitol in a ratio by weight of between approximately 70:30 and approximately 97:3,
   (iii) introducing said mixture into a fluidised bed granulator,
   (iv) granulating said mixture under the following conditions:
      (a) spraying a quantity of pure water of between 5% and 35% by weight with respect to the weight of said mixture, and
      (b) introducing air at a temperature between 65° C. and 75° C. with a moisture content of less than 5000 ppm for a period of time of from 20 minutes to 30 minutes.

2. The process according to claim 1, wherein said mannitol has an average particle size of less than 100 μm and said sorbitol has an average particle size of between 200 μm and 250 μm.

3. The process according to claim 1, wherein said mixture has an average particle size of less than 200 μm.

4. The process according to claim 1, wherein said mixture has a ratio by weight between said mannitol and said sorbitol between approximately 80:20 and approximately 95:5.

5. The process according to claim 1, wherein the quantity of water is between 15% and 25% by weight with respect to the weight of the mixture.

6. The process according to claim 1, wherein said air has a moisture content equal to or lower than 1000 ppm.

7. The process according to claim 3, wherein said mixture has an average particle size of between 100 μm and 150 μm.

\* \* \* \* \*